US00PP17098P3

(12) United States Plant Patent
Noack

(10) Patent No.: US PP17,098 P3
(45) Date of Patent: Sep. 12, 2006

(54) GROUND COVER ROSE PLANT NAMED 'NOA97400A'

(50) Latin Name: *Rosa hybrida*
Varietal Denomination: NOA97400A

(76) Inventor: Reinhard Noack, Im Fenne 54, 33334 Gütersloh (DE)

( * ) Notice: Subject to any disclaimer, the term of this patent is extended or adjusted under 35 U.S.C. 154(b) by 0 days.

(21) Appl. No.: 11/043,094

(22) Filed: Jan. 27, 2005

(65) Prior Publication Data

US 2005/0183175 P1 Aug. 18, 2005

(30) Foreign Application Priority Data

Feb. 14, 2004 (DE) ..... ROS2408

(51) Int. Cl.
*A01H 5/00* (2006.01)

(52) U.S. Cl. ..... Plt./105

(58) Field of Classification Search ..... Plt./105, Plt./106, 146
See application file for complete search history.

*Primary Examiner*—Kent Bell
*Assistant Examiner*—June Hwu
(74) *Attorney, Agent, or Firm*—Buchanan Ingersoll PC

(57) ABSTRACT

A new and distinct variety for Ground Cover Rose plant is provided which forms on a substantially continuous basis sprays of attractive bright amber and cream-orange blossoms with the reproductive organs commonly being visible at the center. The blossoms open on a reliable basis and retain their attractiveness upon aging. The new variety initially exhibits a dense and upright growth habit that changes to a spreading growth habit during the second year. The foliage is dark green and glossy and contrasts well with the blossom coloration. The surfaces of leaves commonly are somewhat curled and partially closed. The blossom petals commonly detach cleanly upon full maturity. The plant propagates well from cuttings and by budding. Excellent resistance to Blackspot, Powdery Mildew, and Rust are displayed, and the plant is particularly well suited for growing as an attractive ornamental ground cover in the landscape.

2 Drawing Sheets

Figure 1:
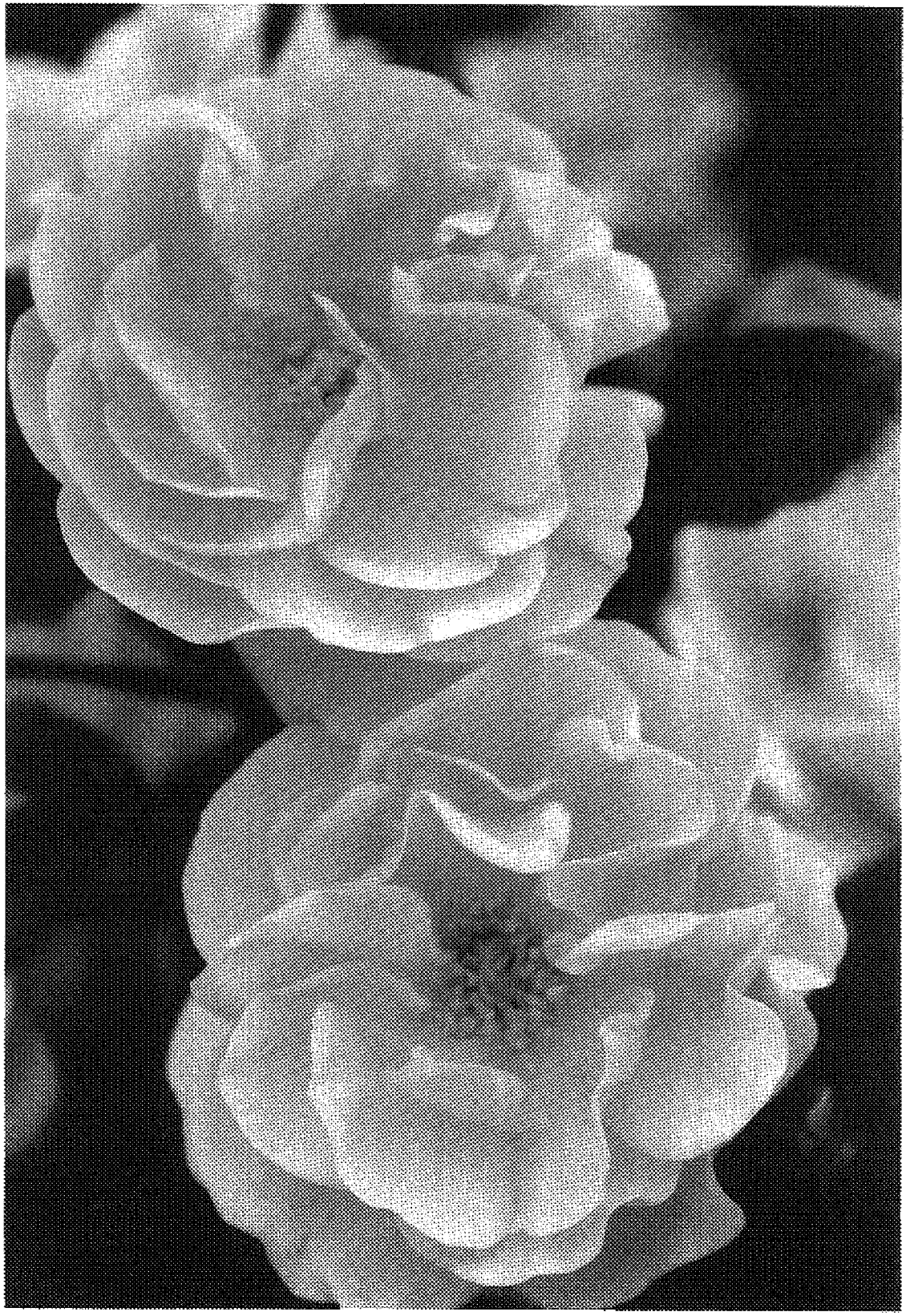

Botanical/commercial classification: *Rosa hybrida*/ Ground Cover Rose Plant.
Varietal denomination: cv. 'NOA97400A'.

SUMMARY OF THE INVENTION

Ground Cover rose plants are known and are being used to advantage in an increasing number of landscape plans and home gardens. However, there remains a need for additional varieties of Ground Cover roses with the demand being the greatest for those having highly attractive blossoms in combination with good disease resistance.

The new variety of *Rosa hybrida* Ground Cover rose plant of the present invention was created at Gütersloh, Germany, by artificial pollination wherein two parents were crossed which previously had been studied in the hope that they would contribute the desired characteristics. The female parent (i.e., the seed parent) was the 'Noatraum' variety (U.S. Plant Pat. No. 7,282). The 'Noatraum' variety sometimes is identified as FLOWER CARPET PINK and is marketed in Europe under the HEIDETRAUM trademark. The male parent (i.e., the pollen parent) was an unnamed and unreleased seedling maintained by Noack Rosen at Gütersloh, Germany (non-patented in the United States). The parentage of the new variety can be summarized as follows:

'Noatraum'×Unnamed Seedling.

The seeds resulting from the above pollination were sown and small plants were obtained which physically and biologically differ from each other. Selective study resulted in the identification of a single plant to the new variety.

It is found that the new variety of Ground Cover rose plant possesses the following combination of characteristics:

(a) forms in sprays attractive long-lasting bright amber and cream-orange blossoms with the reproductive organs commonly being visible at the center,
(b) initially exhibits a dense and upright growth habit that changes to a spreading growth habit during the second year,
(c) forms attractive glossy dark green foliage that contrasts well with the blossoms wherein the surfaces of the leaflets commonly are somewhat curled and partially closed,
(d) exhibits excellent disease resistance with respect to Blackspot, Powdery Mildew, and Rust, and
(e) is particularly well suited for growing as attractive ornamentation in the landscape.

The new variety meets the needs of the horticultural industry and can be grown to advantage as an attractive ornamental ground cover in parks, gardens, public areas, and residential landscapes.

The new variety of the present invention readily can be distinguished from its ancestors. For instance, the 'Noatraum' female parent displays pink blossoms, and the unnamed male parent displays red-purple blossoms and smaller foliage.

Also, the new variety of the present invention can be distinguished from similar Ground Cover varieties, such as the 'Korsoalgu' variety (non-patented in the United States) and the 'Korpatetopf' variety (non-patented in the United States) by an inspection of the blossom coloration. More specifically, the blossoms of the 'Korsoalgu' variety are Yellow-Orange Group 19A in coloration and those of the 'Korpatetopf' variety are Yellow-Orange Group 20B in coloration.

The new variety of the present invention beginning in 2000 has been asexually reproduced by the rooting of cuttings, and by budding. Such asexual reproduction as performed at Gütersloh, Germany, has demonstrated that the characteristics of the new variety are firmly fixed and stable and are strictly transmissible from one generation to another. The new variety asexually reproduces in a true to type manner from one generation to another.

The new variety of the present invention has been named 'NOA97400A'.

BRIEF DESCRIPTION OF THE PHOTOGRAPHS

The accompanying photographs show as nearly true as it is reasonably possible to make the same, in color illustrations of this character, typical specimens of the new variety while growing outdoors. The illustrated rose plants were photographed during July, 2004, while growing in a field at Gütersloh, Germany. Such plants had been budded approximately one and one-half years earlier.

FIG. 1 illustrates a close view of the attractive amber and cream-orange blossoms of the new variety wherein the reproductive organs are visible at the center.

Figure 2:
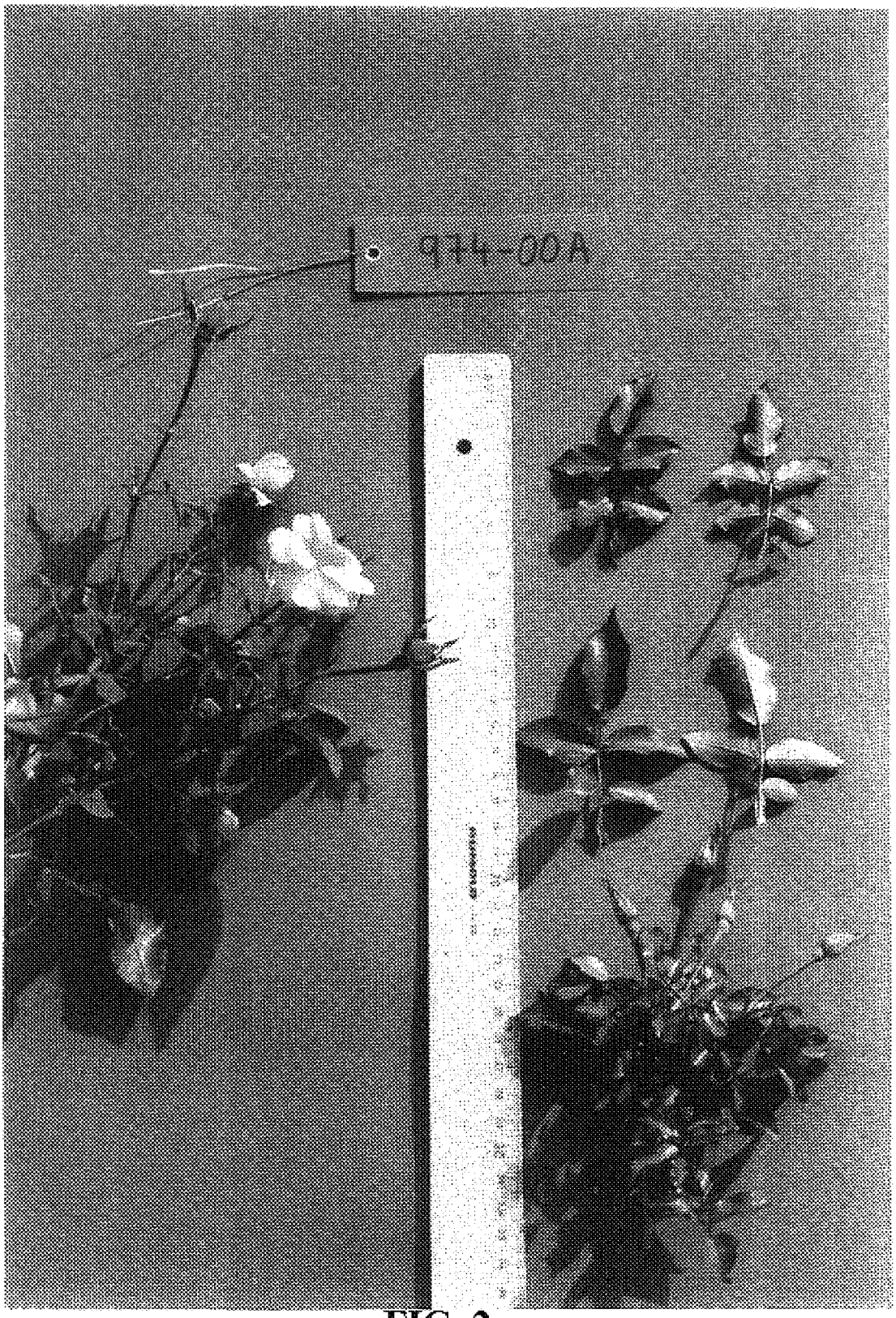

FIG. 2 illustrates at the right the upper and under surfaces of typical leaves, buds and glossy foliage, and at the left buds and flowers in various stages of opening as well as additional foliage. The configuration of the somewhat curled and partially closed leaflets is illustrated. Dimensions in centimeters are included at the center.

DETAILED DESCRIPTION

The chart used in the identification of the colors is that of The Royal Horticultural Society (R.H.S. Colour Chart) of London, England. Color terminology in common terms sometimes is included as an aid to the reader. Such color terminology is to be accorded its customary dictionary significance. The description is based on the observation of typical specimens of the new variety while growing outdoors during July at Gütersloh, Germany.

Class: Ground Cover.

Plant:

*Form.*—Vigorous, young plants exhibit a dense and upright growth habit, and with further maturity spread to form a compact bush that serves well as ground cover with dense foliage.

*Height.*—Approximately 70 cm on average.

*Width.*—Approximately 70 cm on average.

Branches:

*Color.*—Young stems: medium green (Green Group 138B) with a smooth surface. Adult wood: darker green (Green Group 138A) than the young stems and with a smooth surface.

*Thorns.*—Size: medium, approximately 5 mm in length on average, and slightly curved downward on the upper surface, and concave on the under surface. Position: irregular. Color: initially Greyed-Red Group 181A when immature and changing to Greyed-Orange Group 172A at maturity. Quantity: typical for a Ground Cover rose plant.

Leaves:

*Stipules.*—Green Group 138B in coloration, smooth to slightly rough in texture, and approximately 0.4×5 mm in size.

*Leaflets.*—Number: commonly 5, and sometimes 7. Configuration: generally elliptical with a narrowly pointed apex, and commonly curled upwards at the margin thereby giving the leaves partially closed appearance. Quantity: very abundant. Size: commonly approximately 2.5 to 3 cm in length and approximately 1.5 cm in width, with the size being influenced by growing conditions. Serration: slightly serrate. Color: (young foliage): Upper surface: Green Group 138A. Under surface: Green Group 138B. Color: (adult foliage): Upper surface: Green Group 137A. Under surface: Green Group 137C. General appearance: dense, dark green foliage that is glossy on the upper surface and matte on the under surface with the curled nature of the leaves being readily apparent. Texture: leathery. Petiole: approximately 1.5 cm in length when mature, smooth to slightly rough in texture, and Yellow-Green Group 144A in coloration.

Inflorescence:

*Number of flowers.*—In clusters of flowers commonly numbering approximately 2 to 3 as a spray.

*Peduncle.*—Soft green in coloration with anthocyanin coloration of Greyed-Red Group 182A, approximately 3 cm in length, and approximately 0.5 cm in diameter.

*Sepals.*—Shape: commonly extend well beyond the petals of the bud, pointed, somewhat rough in texture, approximately 2 cm in length on average, commonly with weak to medium foliaceous appendages, and Yellow-Green Group 144A initially with some Greyed-Purple Group 184B in coloration.

*Buds.*—Color when opening: Yellow-Orange Group 17A to 17D on the upper surface and Yellow-Orange Group 16C and 16D on the under surface.

*Flower.*—Form: somewhat flattened. Appearance: smooth on both petal surfaces. Diameter: approximately 5 cm on average. Color (when opening begins): Upper surface: predominantly Yellow-Orange Group 17A. Color (when blooming): Upper surface: Yellow-Orange Group 17A. The bright yellow coloration of pollen and the reproductive organs commonly is visible at the center. Under surface: predominantly Yellow-Orange Group 16C and 16D. Color (at the end of opening): Upper surface: bright amber and cream-orange coloration that is predominantly Yellow-Orange Group 17A. Fragrance: none. Lasting quality: very good. Petal form: broad, fan-shaped, curved with a somewhat indented central area and margin areas that are slightly curved towards the center. Petal number: commonly approximately 15 on average. Petal size: with a rounded tip, approximately 4 cm in length, and approximately 3 to 4 cm in width. Petal arrangement: generally arranged in a regular pattern with overlapping edges. Petal drop: good with the petals detaching cleanly upon fully maturity. Stamens: approximately 30 in number, and regularly arranged around the styles. Filaments: approximately 1 cm in length, and yellow (Yellow-Orange Group 15A) in coloration. Anthers: approximately 3 to 4 mm in size. Pollen: yellow (Yellow-Orange Group 15B) in coloration. Pistil: one per flower. Stigmas: approximately 3 to 4 mm in size, and yellow (Yellow-Orange Group 17B) in coloration. Styles: commonly less than 1 cm in length, thin and regularly arranged at the center, and Yellow-Orange Group 17B in coloration. Hips: generally globular in shape, smooth in texture, approximately 2 cm in length, and initially green in coloration changing to red-orange with maturity. Seeds: round to oblong in shape, approximately 2 mm in length, and Yellow-Orange Group 18A in coloration. Lastingness: commonly approximately 5 days on the plant depending upon environmental conditions, and approximately 3 days when cut and placed in a vase. Receptacle: generally round to oval, commonly with some constriction at the middle, smooth in texture, approximately 1 to 1.5 cm in length, and Greyed-Red Group 181B in coloration.

Development:

*Vegetation.*—Strong, compact, and vigorous.

*Blooming.*—Substantially continuous throughout the season in large sprays.

*Aptitude to bear fruit.*—Slight.

*Winter hardiness.*—Good.

*Resistance to diseases.*—Excellent with respect to Blackspot, Powdery Mildew, and Rust.

I claim:

1. A new and distinct Ground Cover Rose plant characterized by the following combination of characteristics:

(a) forms in sprays attractive long-lasting bright amber and cream-orange blossoms with the reproductive organs commonly being visible at the center, (b) initially exhibits a dense and upright growth habit that changes to a spreading growth habit during the second year, (c) forms attractive glossy dark green foliage that contrasts well with the blossoms wherein the surfaces of the leaflets commonly are somewhat curled and partially closed, (d) exhibits excellent disease resistance with respect to Blackspot, Powdery Mildew, and Rust, and (e) is particularly well suited for growing as attractive ornamentation in the landscape;

substantially as illustrated and described.

* * * * *